(12) United States Patent
Irisawa

(10) Patent No.: US 10,241,272 B2
(45) Date of Patent: Mar. 26, 2019

(54) INSERT AND ATTACHMENT MEMBER

(71) Applicant: FUJIFILM Corporation, Tokyo (JP)

(72) Inventor: Kaku Irisawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/042,458

(22) Filed: Jul. 23, 2018

(65) Prior Publication Data

US 2018/0329142 A1 Nov. 15, 2018

Related U.S. Application Data

(63) Continuation of application No. PCT/JP2017/001462, filed on Jan. 18, 2017.

(30) Foreign Application Priority Data

Jan. 25, 2016 (JP) .................. 2016-011603

(51) Int. Cl.
*G02B 6/26* (2006.01)
*A61B 8/13* (2006.01)
(Continued)

(52) U.S. Cl.
CPC ............. *G02B 6/262* (2013.01); *A61B 8/13* (2013.01); *A61B 5/6848* (2013.01); *A61B 10/0233* (2013.01); *A61B 2017/3413* (2013.01)

(58) Field of Classification Search
CPC ....... G02B 6/262; A61B 8/13; A61B 10/0233; A61B 5/6848; A61B 2017/3413
See application file for complete search history.

(56) References Cited

U.S. PATENT DOCUMENTS 5,725,514 A * 3/1998 Grinblat .................. A61F 9/007
128/898
6,224,566 B1 * 5/2001 Loeb ................. A61M 25/0084
604/20

(Continued)

FOREIGN PATENT DOCUMENTS

JP 2013-13713 A 1/2013
JP 2015-37519 A 2/2015
(Continued)

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2017/001462, dated Aug. 9, 2018, with English translation.
(Continued)

*Primary Examiner* — Ryan A Lepisto
(74) *Attorney, Agent, or Firm* — Birch, Stewart, Kolasch & Birch, LLP

(57) ABSTRACT

An optical fiber is inserted into an inside portion of a hollow tube of an insert and guides light emitted from a light source. A base end section includes an optical fiber insertion part used for inserting the optical fiber. An optical fiber fixing member fixes the optical fiber at a position spaced from a distal end of the optical fiber. The optical fiber insertion part has a first portion into which the optical fiber fixing member is inserted. The first portion has at least three protrusions protruding toward the center at positions spaced from each other in a circumferential direction. A size of the optical fiber fixing member in a direction perpendicular to an insertion direction into the first portion is larger than that of an inside portion of the first portion, and the optical fiber fixing member is harder than the first portion.

15 Claims, 6 Drawing Sheets

(51) Int. Cl.
    *A61B 17/34*     (2006.01)
    *A61B 5/00*     (2006.01)
    *A61B 10/02*     (2006.01)

(56) References Cited

U.S. PATENT DOCUMENTS

| | | | |
|---|---|---|---|
| 2014/0121538 A1* | 5/2014 | Hendriks | A61B 5/0084 600/478 |
| 2015/0297092 A1 | 10/2015 | Irisawa | |
| 2016/0135689 A1 | 5/2016 | Murakoshi | |
| 2017/0112386 A1* | 4/2017 | Irisawa | A61B 8/13 |
| 2017/0139155 A1* | 5/2017 | Tong | G02B 6/3861 |
| 2018/0116630 A1* | 5/2018 | Dykes | A61B 8/12 |

FOREIGN PATENT DOCUMENTS

| | | |
|---|---|---|
| JP | 2015-43969 A | 3/2015 |
| WO | WO 2014/109148 A1 | 7/2014 |

OTHER PUBLICATIONS

International Search Report (Form PCT/ISA/210) for International Application No. PCT/JP2017/001462, dated Apr. 18, 2017, with English translation.

\* cited by examiner

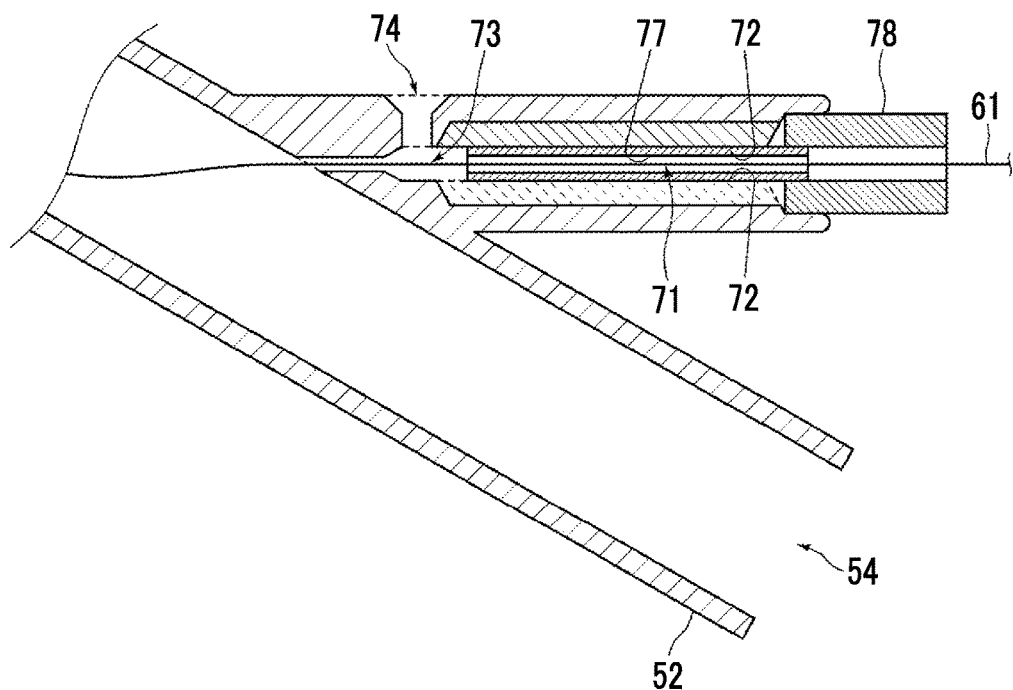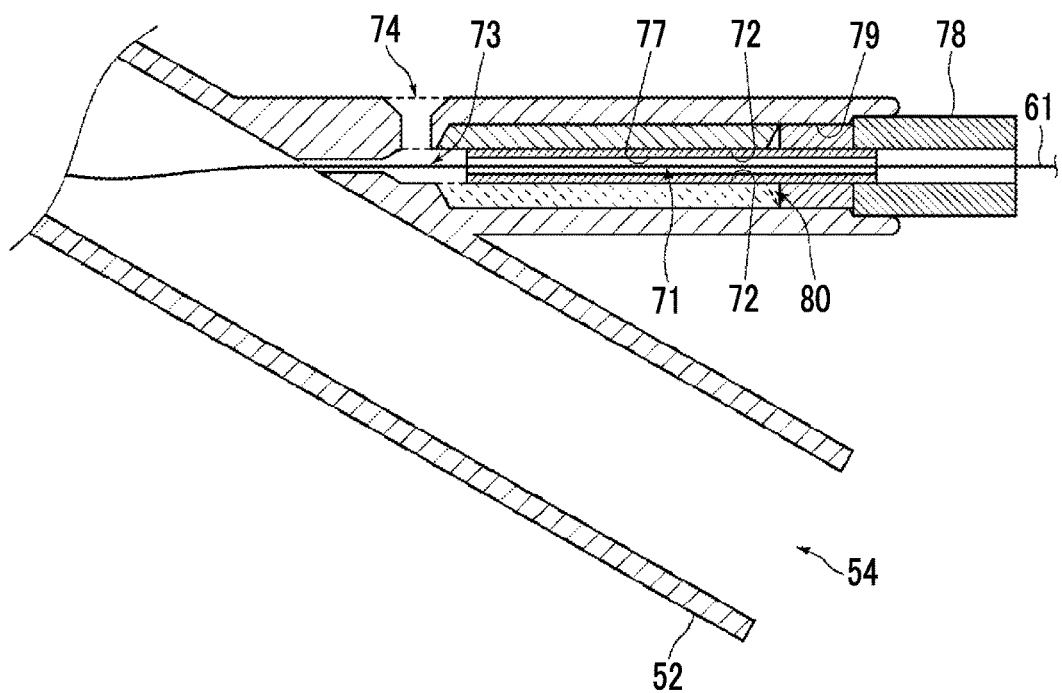

INSERT AND ATTACHMENT MEMBER

CROSS-REFERENCE TO RELATED APPLICATIONS

This application is a continuation application of International Application No. PCT/JP2017/001462, filed Jan. 18, 2017, the disclosure of which is incorporated herein by reference in its entirety. Further, this application claims priority from Japanese Patent Application No. 2016-011603, filed Jan. 25, 2016, the disclosure of which is incorporated herein by reference in its entirety.

BACKGROUND

1. Technical Field

The present invention relates to an insert and specifically relates to an insert that includes a hollow tube and of which at least a portion is inserted into a subject. The present invention relates to an attachment member that is formed to be engageable with a hollow tube.

2. Related Art

An ultrasonic examination method is known as a kind of image inspection method that may non-invasively inspect the state inside a living body. In the ultrasonic examination, an ultrasound probe that may transmit and receive ultrasonic waves is used. In a case where ultrasonic waves are transmitted from an ultrasound probe to a subject (living body), the ultrasonic waves advance inside the living body, and the ultrasonic waves are reflected on a tissue interface. The reflected ultrasonic waves are received by an ultrasound probe, and a distance is calculated based on time until the reflected ultrasonic waves return to the ultrasound probe, so as to image the state of the inside.

Photoacoustic imaging for imaging the inside of a living body by using the photoacoustic effect is known. Generally, in the photoacoustic imaging, a living body is irradiated with pulsed laser light. In the inside portion of the living body, the living tissue absorbs energy of the pulsed laser light, and ultrasonic waves (photoacoustic waves) are generated due to adiabatic expansion by the energy. In a case where photoacoustic waves are detected with an ultrasonic probe or the like, and a photoacoustic image is formed based on the detection signal, the visualization in the living body based on the photoacoustic wave may be performed.

Here, JP2015-037519A discloses that photoacoustic waves are generated in an insert inserted into a subject, and a photoacoustic image is generated based on the photoacoustic waves. In JP2015-037519A, light emitted from a light source is guided to a portion near a distal end of a puncture needle that is an insert using light guiding means such as an optical fiber. A light absorbing member or the like is arranged near the distal end of a puncture needle, and the light absorbing member is irradiated with light from a light emission end of the optical fiber. According to this light irradiation, photoacoustic waves are generated near the distal end of the puncture needle. The photoacoustic waves are detected by using a probe, and the photoacoustic image is generated based on the detected photoacoustic waves, so as to confirm the position near the distal end of the puncture needle using the photoacoustic image.

SUMMARY

In JP2015-037519A, in a case where a shielding object is present between the generation source and the probe of the photoacoustic waves, the photoacoustic waves are damped by the shielding object, and the intensity of the photoacoustic waves detected by the probe is weakened. In order to maximize the intensity of the photoacoustic waves detected by the probe, it is necessary to accurately align the light emitting end of light guide means such as an optical fiber to a portion near the distal end of the puncture needle having an opening.

For example, it is considered that an optical fiber is inserted into a needle tube of a puncture needle having a length of about several tens of mm from an optical fiber insertion part (insertion opening) provided in the base end section, so as to align the distal end of the optical fiber to a portion near the distal end of the puncture needle. In this case, the position of the distal end of the optical fiber may be finely adjusted by finely adjusting the insertion length of the optical fiber.

The distal end of the optical fiber may be fixed at a desired position by fixing the optical fiber to the insertion opening by using an adhesive or the like, after the insertion length of the optical fiber is finely adjusted. However, in a case where the inner diameter of the insertion opening of the optical fiber is longer than the diameter of the optical fiber, in a case where the hand is released from the optical fiber or the like before the optical fiber is fixed, the optical fiber may move so as to change the insertion length of the optical fiber into the hollow tube. In a case where the insertion length of the optical fiber is changed, the position of the distal end of the optical fiber moves from the position in a case of the adjustment.

In view of the above, an object of the present invention is to provide an insert and an attachment member that is formed to be capable of suppressing the change of the insertion length of an optical fiber after the insertion length of the optical fiber to a hollow tube is adjusted.

In order to achieve the above object, the present invention provides an insert comprising: a hollow tube of which at least a portion is inserted into a subject; an optical fiber that is inserted into an inside portion of the hollow tube and guides light emitted from a light source; a base end section including an optical fiber insertion part used for inserting the optical fiber; a light absorbing member that absorbs light guided by the optical fiber in a case of being irradiated with the light and generates a photoacoustic wave; an optical fiber fixing member that fixes the optical fiber at a position spaced from a distal end of the optical fiber and inserted into the optical fiber insertion part, in which the optical fiber insertion part includes a first portion into which the optical fiber fixing member is inserted and which has at least three protrusions protruding toward the center at positions spaced from each other in a circumferential direction, and a size of the optical fiber fixing member in a direction perpendicular to an insertion direction into the first portion is larger than that of an inside portion of the first portion, and the optical fiber fixing member is fixed by the at least three protrusions of the first portion.

In the insert of the present invention, it is preferable that a size of a cross section of the optical fiber fixing member in the direction perpendicular to the insertion direction is larger than that of a diagram that is circumscribed with the at least three protrusions and is similar to a shape of the cross section of the optical fiber fixing member in the direction perpendicular to the insertion direction.

In the insert of the present invention, it is preferable that the optical fiber insertion part has an axis extending along a predetermined direction. In this case, it is preferable that an insertion amount of the optical fiber fixing member into the first portion in the direction of the axis is capable of being adjusted.

In the insert of the present invention, it is preferable that the at least three protrusions extend along the insertion direction of the optical fiber.

In the insert of the present invention, the optical fiber insertion part may further include an adhesive injection port provided deeper than the first portion in the insertion direction of the optical fiber.

In the insert of the present invention, the optical fiber fixing member may be fixed in the optical fiber insertion part with an adhesive injected from the adhesive injection port.

In the insert of the present invention, it is preferable that Young's modulus of the optical fiber fixing member is the same as that of the first portion or higher than that of the first portion.

In the insert of the present invention, the optical fiber fixing member may be formed of at least one of a metallic material, a hard resin material, or a ceramic material.

In the insert of the present invention, the at least three protrusions may be formed of a resin material.

The insert of the present invention further comprises a metal tube into which the optical fiber fixing member is inserted.

In the insert, the optical fiber insertion part may include a second portion having a size larger than the size of the optical fiber fixing member on a near side of the first portion in the insertion direction of the optical fiber. In this case, the metal tube may be inserted into the second portion.

It is preferable that a size of the inside portion of the metal tube is larger than the size of the optical fiber fixing member.

In the insert of the present invention, the hollow tube may have an opening at a distal end, and the distal end of the hollow tube may be sharpened at an acute angle.

In the insert of the present invention, it is preferable that a length of the first portion in the insertion direction of the optical fiber is longer than that of the portion of the distal end of the hollow tube which is sharpened at an acute angle.

The present invention also provides an attachment member which is engageable with a hollow tube of which at least a portion is inserted into a subject, the attachment member comprising: an optical fiber that is inserted into an inside portion of the hollow tube in a case where the hollow tube is engaged and guides light emitted from a light source; a base end section including an optical fiber insertion part used for inserting the optical fiber; and an optical fiber fixing member that fixes the optical fiber at a position spaced from a distal end of the optical fiber and is inserted into the optical fiber insertion part, the optical fiber insertion part includes a first portion into which the optical fiber fixing member is inserted and which has at least three protrusions protruding toward the center at positions spaced from each other in a circumferential direction, and a size of the optical fiber fixing member in a direction perpendicular to an insertion direction into the first portion is larger than that of an inside portion of the first portion, and the optical fiber fixing member is fixed by the at least three protrusions of the first portion.

An insert and an attachment member of the present invention may suppress a change in an insertion length of an optical fiber after adjusting an insertion length of the optical fiber with respect to the hollow tube.

BRIEF DESCRIPTION OF THE DRAWINGS

Exemplary embodiments according to the technique of the present disclosure will be described in detail based on the following figures, wherein:

FIG. 7 is a cross sectional view illustrating a base end section in a state in which an optical fiber is inserted into an optical fiber insertion part;

FIG. 8 is a cross sectional view illustrating a base end section of a puncture needle of a second embodiment of the present invention;

DETAILED DESCRIPTION

Figure 1:
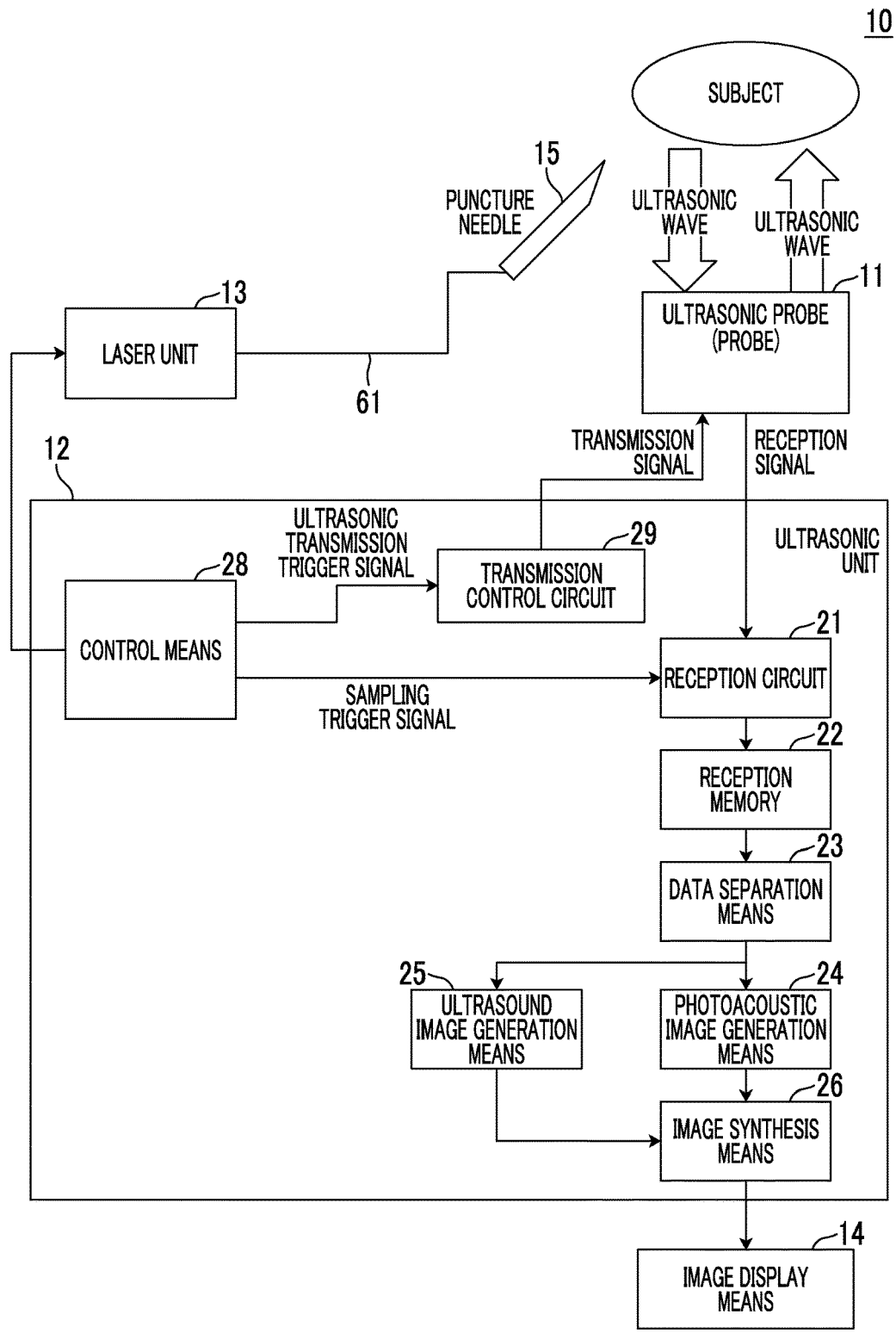
FIG. 1 is a block diagram illustrating a photoacoustic image generating device used in an insert according to a first embodiment of the present invention.

Hereinafter, embodiments of the present invention will be described in detail with reference to the drawings. FIG. 1 illustrates a photoacoustic image generating device used in an insert according to a first embodiment of the present invention. A photoacoustic image generating device (photoacoustic image diagnostic device) 10 includes a probe (ultrasound probe) 11, an ultrasonic unit 12, a laser unit 13, and a puncture needle 15. According to the embodiment of the present invention, ultrasonic waves are used as the acoustic waves, but the present invention is not limited to ultrasonic waves. An acoustic wave of an audible frequency may be used as long as an appropriate frequency may be selected according to a subject to be examined, measurement conditions, or the like.

The laser unit 13 is a light source. The laser unit 13 is, for example, a laser diode light source (semiconductor laser light source). Otherwise, the laser unit 13 may be a light amplification type laser light source using a laser diode light source as a seed light source. A type of the laser light source used in the laser unit 13 is not particularly limited, and a solid-state laser light source using, for example, yttrium-aluminum-garnet (YAG), alexandrite, or the like may be used for the laser unit 13. The laser light emitted from the laser unit 13, for example, is guided to the puncture needle 15 by using light guiding means such as an optical fiber 61. A light source other than the laser light source may be used.

Figure 2:
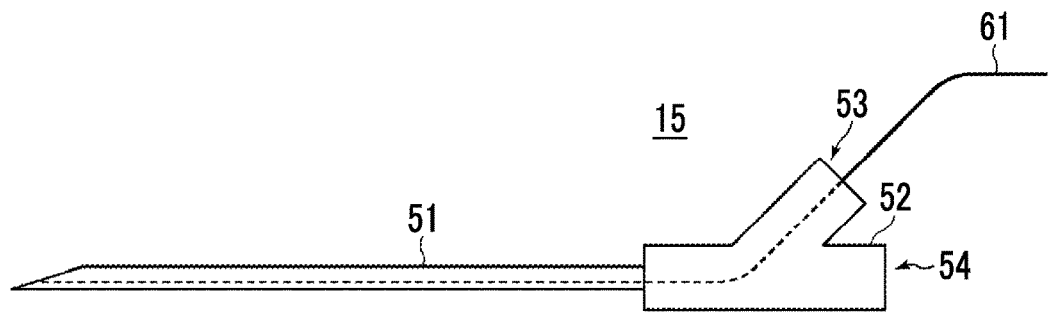
FIG. 2 is a side view illustrating a puncture needle.

According to the present embodiment, the puncture needle 15 that includes a hollow tube and may be used for injection of medicine or the like is considered as an insert of which at least a portion is inserted into the subject is considered. FIG. 2 illustrates the puncture needle 15. The puncture needle 15 has a needle tube 51 and a base end section (needle base) 52. The needle tube 51 is a hollow tube that has an opening at a distal end and has a lumen inside. The needle tube 51, for example, is formed of metal such as stainless steel. The needle tube 51, for example, may be made of a fluororesin material such as polytetrafluoroethylene. The base end section 52, for example, is formed of a resin material such as polypropylene, polycarbonate, and polyester. The needle tube 51, for example, is adhered to the distal end side of the base end section 52 with an adhesive such as an epoxy resin.

The base end section 52 has an optical fiber insertion part (optical fiber insertion port) 53 and a medicine injection portion (medicine injection port) 54. The optical fiber insertion part 53, for example, has a hole having a diameter of about 4 mm. The medicine injection portion 54, for example, has a hole having a diameter of about 6 mm to 8 mm. The optical fiber 61 that guides light emitted from the laser unit 13 is inserted into the inside portion of the needle tube 51 through the optical fiber insertion part 53. The optical fiber 61 is inside of the needle tube 51 and, for example, it is preferable that the optical fiber is stored in a tube formed of a resin material such as polyimide or is covered with a resin material to be protected.

The medicine injection portion 54 is an injection port of liquid medicine. As the medicine to be used, for example, anesthetic, infusion, anticancer drug, ethanol, a contrast medium, and physiological saline may be considered. A syringe, a liquid transfusing tube, and the like are attached to the medicine injection portion 54. The medicine injection portion 54 may be used not only for injecting medicine but also for taking out liquid such as blood or body fluid from the subject.

Figure 3:
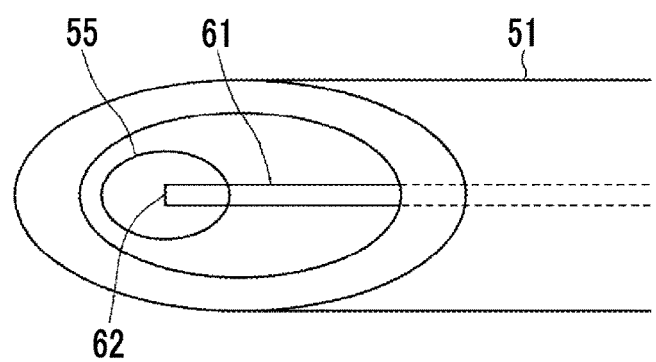
FIG. 3 is a front view illustrating a front end section of a needle tube in a puncture needle.

FIG. 3 illustrates a front end section of the needle tube 51. The needle tube 51 has an opening at a distal end. The distal end of the needle tube 51 is sharpened at an acute angle. A light emitting portion 62 and a light absorbing member 55 of the optical fiber 61 is arranged at the front end section of the needle tube 51. The light emitting portion 62 is formed by an end face on the light advancing side as seen from the laser unit 13 of the optical fiber 61. The light absorbing member 55 is irradiated with the light guided by the optical fiber 61 from the light emitting portion 62. The diameter of the optical fiber, for example, is 130 μm, and for example, the light absorbing member 55 is irradiated with 2 μJ of laser light from the light emitting portion 62.

The light absorbing member 55 absorbs light emitted from the light emitting portion 62 and generates photoacoustic waves. For example, an epoxy resin, a polyurethane resin, a fluororesin, or a silicone rubber, which is mixed with a black pigment may be used for the light absorbing member 55. Otherwise, metal or oxide having light absorption properties with respect to the wavelength of laser light may be used for the light absorbing member 55. For example, as the light absorbing member 55, oxide such as iron oxide, chromium oxide, or manganese oxide having high light absorption properties with respect to the wavelength of the laser light may be used. Otherwise, metal such as Ti, Pt, solder, or welded stainless steel may be used as the light absorbing member 55. An adhesive may be further applied on the light absorbing member 55 and cured such that the distal end thereof is fixed on to an inner wall of the needle tube 51.

The light absorbing member 55 provided around the light emitting portion 62 is irradiated with at least a portion of the light emitted from the light emitting portion 62. In a case where the light absorbing member 55 absorbs the irradiated light, a photoacoustic wave is generated at a distal end of the puncture needle. The light absorbing member 55 exists near the distal end of the puncture needle 15, and the photoacoustic waves may be generated at a point of the distal end of the puncture needle 15. The length of the generation source (sound source) of the photoacoustic wave is sufficiently shorter than compared with the entire length of the puncture needle, and the sound source may be regarded as a point sound source. Here, the expression "near the distal end of the puncture needle 15" refers to a position at which a photoacoustic wave capable of imaging the position of the distal end of the puncture needle 15 with the accuracy necessary for a puncture operation may be generated in a case where the light emitting portion 62 and the light absorbing member 55 are arranged at this position. For example, the expression refers to a portion in the range of 0 mm to 3 mm from the distal end having the opening of the puncture needle 15 to the base end section side.

Figure 4:
FIG. 4 is a drawing illustrating an optical fiber inserted from an optical fiber insertion part.

FIG. 4 illustrates the optical fiber 61 inserted from the optical fiber insertion part 53 (see FIG. 2). The light absorbing member 55 is attached to an end portion on a distal side seen from the light source of the optical fiber 61. The optical fiber 61 is inserted into an optical fiber insertion opening from the light absorbing member 55 side. The light absorbing member 55 may not be attached to a distal end of the optical fiber 61 before the insertion of the optical fiber 61. After the optical fiber 61 is inserted into the needle tube 51, the light absorbing member 55 may be attached to the distal end of the optical fiber 61. In this case, the light absorbing member 55 may also function as a member for fixing the optical fiber 61 to the inner wall of the needle tube 51.

An optical fiber fixing member 77 fixes the optical fiber 61 to a position spaced from the distal end (the light emitting portion 62 of FIG. 3) of the optical fiber 61. Here, the expression "the position spaced from the distal end of the optical fiber 61", for example, refers to a position separated from the distal end of the optical fiber 61 by a predetermined distance. It is preferable that the predetermined distance is substantially equal to the length from the distal end of the needle tube 51 to the optical fiber insertion part 53. In a case where the optical fiber 61 is fixed at a position at which the optical fiber fixing member 77 is spaced from such a distance, in a case where the distal end of the optical fiber 61 comes close to the distal end of the needle tube 51, the optical fiber fixing member 77 is inserted into the inside portion of the optical fiber insertion part 53.

The optical fiber fixing member 77, for example, is formed of at least one of a metallic material, a hard resin material, and a ceramic material. The optical fiber fixing member 77, for example, has a through hole in a center portion, and the optical fiber 61 is inserted into the through hole. The position at which the optical fiber 61 inserted into the through hole is fixed to the optical fiber fixing member 77 is determined based on the length of the needle tube 51, and the distance from the optical fiber insertion part 53 to the end portion of the needle tube 51 on the base end section 52 side.

An optical connector 47 connected to an optical connector provided in the laser unit 13 is attached to an end portion of the optical fiber 61 on the light source side. A sheath 63 is a tube having flexibility and protects an optical fiber between the optical fiber fixing member 77 and the optical connector 47. It is preferable that the optical fiber 61 is covered with a polyimide resin or the like or protected by another protection tube in a predetermined range from the optical fiber fixing member 77 on the laser unit 13 side.

Figure 5:
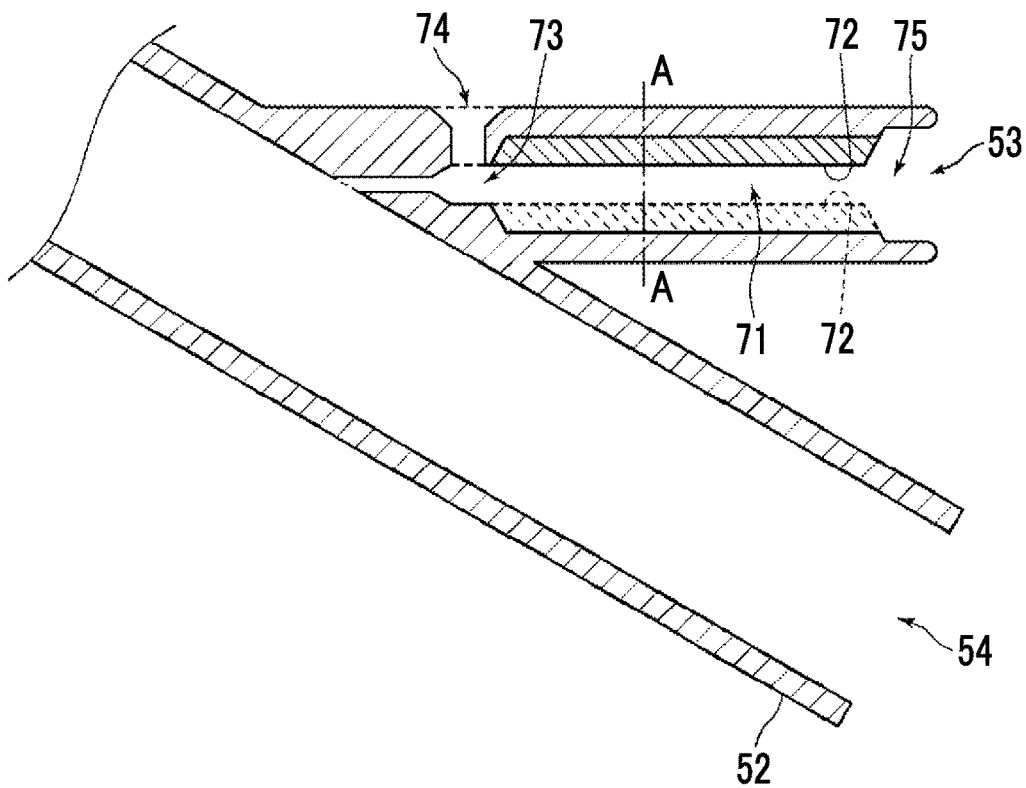
FIG. 5 is a cross sectional view illustrating a base end section of a puncture needle according to the first embodiment of the present invention.
Figure 6:
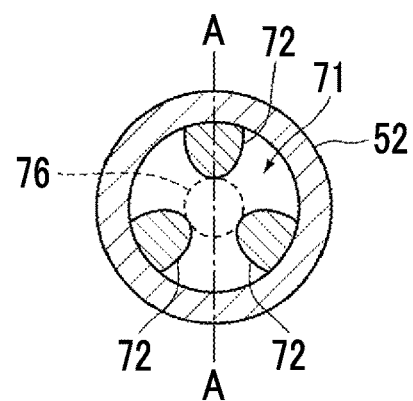
FIG. 6 is a cross sectional view illustrating a cross section taken along line A-A of FIG. 5.

In the puncture needle 15 of the present embodiment, in order to accurately align the light emitting portion 62 of the optical fiber 61 near the distal end of the needle tube 51, the optical fiber insertion part 53 is formed such that the optical fiber insertion length may be adjusted. FIG. 5 illustrates the cross section of the base end section 52 of the puncture needle 15 according to the first embodiment of the present invention. FIG. 6 illustrates a cross section taken along line A-A of FIG. 5. FIG. 7 illustrates a cross section of the base end section 52 in a state in which the optical fiber 61 is inserted into the optical fiber insertion part 53. As illustrated in FIG. 5, the optical fiber insertion part 53 has a through hole that communicates with the needle tube 51 (not illustrated in FIG. 5). The medicine injection portion 54 has a through hole that communicates with the needle tube 51, and the optical fiber insertion part 53 and the medicine injection portion 54 are merged in the inside portion of the base end section 52.

The optical fiber insertion part 53 has an axis extending along a predetermined direction. The optical fiber insertion part 53 has a first portion 71 into which the optical fiber fixing member 77 (see FIG. 4) is inserted. The first portion 71 has a protrusion 72 that protrudes toward the center of the optical fiber insertion part 53. As illustrated in FIG. 6, the first portion 71 has three protrusions 72 at positions spaced from each other in a circumferential direction. The protrusion 72, for example, is formed of a resin material. For example, in a case where a main body portion of the base end section 52 is formed by injection mold, the protrusion 72 is formed in the inside portion of the optical fiber insertion part 53 during the injection mold.

The number of the protrusions 72 in the first portion 71 is not limited to three, the first portion may have four or more protrusions 72. The shape of the cross section of the protrusion 72 is not particularly limited to FIG. 6. The shape of the cross section in a case where the optical fiber insertion part 53 is cut in along the plane perpendicular to the axial direction of the optical fiber insertion part 53 at the position of the first portion 71 is not limited to a circular shape, but may be a polygonal shape such as a square or a hexagon.

Instead of using the protrusion 72 in the first portion 71, the cross section in the first portion 71 may have an oval shape or a polygonal shape such as square or hexagon. In short, in a case where a cross sectional area of the first portion 71 is larger than a cross sectional area of the optical fiber fixing member 77, a protrusion formed in the first portion 71 or a wall surface of the first portion 71 comes into contact with the cross section of the optical fiber fixing member 77 at two or more points, the resistance force is sufficiently generated during the insertion of the optical fiber fixing member 77.

In the first portion 71, the three protrusions 72 respectively extend in the insertion direction of the optical fiber. In the first portion 71, since the protrusion 72 protrudes to the inside portion, the size of the inside portion of the first portion 71 is reduced by the amount of the protrusion. The optical fiber 61 (see FIG. 4) is inserted into the optical fiber insertion part 53 from the distal end side thereof. In a case where the optical fiber 61 is inserted into the needle tube 51 from the optical fiber insertion part 53, the optical fiber fixing member 77 that fixes the optical fiber 61 is inserted into the first portion 71.

According to the present embodiment, the size of the optical fiber fixing member 77 in the direction perpendicular to the insertion direction into the first portion 71 is larger than the size of the inside portion of the first portion 71. For example, the expression "the size is large" means that a diameter is large in a case where the shape is a circle or means that a length of each side is long in a case where the shape is a polygonal shape. Accordingly, the optical fiber fixing member 77 may be fixed by the protrusion 72 of the first portion 71. According to the present embodiment, Young's modulus of the optical fiber fixing member 77 is preferably equal to or higher than Young's modulus of the first portion 71. Accordingly, at least one of at least three of protrusions 72 of the first portion 71 or the optical fiber fixing member 77 is slightly deformed to come into contact with each other, and as a result, the optical fiber fixing member 77 may be fixed by the protrusion 72 of the first portion 71.

According to the present embodiment, the size of the cross section of the optical fiber fixing member 77 in the direction perpendicular to the insertion direction into the first portion 71 is larger than the size of the diagram similar to the shape of the cross section of the optical fiber fixing member 77 that is circumscribed with the three protrusions of the first portion 71 and that is in the direction perpendicular to the insertion direction. For example, a case where the shape of the optical fiber fixing member 77 in the direction perpendicular to the insertion direction into the first portion 71 has a circular shape is considered. In the first portion 71, as illustrated in FIG. 6, a circle 76 that is circumscribed with the three protrusions 72 is considered. In this case, the diameter of the circle 76 is smaller than the outside diameter of the optical fiber fixing member 77. Specifically, for example, in a case where the outside diameter of the optical fiber fixing member 77 is about 1.5mm, the diameter of the circle 76 is set as about 1.45 mm.

According to the present embodiment, in the first portion 71, the optical fiber fixing member 77 is supported by the three protrusions 72. The space on the inner side of the three protrusions 72 in the first portion 71 is narrower than the optical fiber fixing member 77, and thus the optical fiber fixing member 77 is required to be pushed to the first portion 71 in order to insert the optical fiber fixing member 77 into the first portion 71. In a case where the optical fiber fixing member 77 is pushed to the first portion 71, the protrusions 72 are subjected to elastic or plastic deformation, and frictional force is generated between the protrusion 72 and the optical fiber fixing member 77.

According to the present embodiment, the buckling load of the optical fiber fixing member 77 is greater than the frictional force in a case where the optical fiber fixing member 77 is pushed to the first portion 71. Therefore, the position of the optical fiber fixing member 77 in the first portion 71 may be changed, and the insertion amount of the optical fiber fixing member 77 in the optical fiber insertion direction into the first portion 71 may be adjusted. In a case where frictional force works between the optical fiber fixing member 77 and the protrusion 72 in the first portion 71, in a state in which force is not applied to the optical fiber fixing member 77, the optical fiber fixing member 77 may be temporarily fixed to the inside portion of the optical fiber insertion part 53. Here, the expression "being temporarily fixed" means a state of being not completely fixed and being not displaced in the insertion direction even in a case where some force is applied.

According to the present embodiment, in a case where the insertion amount of the optical fiber fixing member 77 is adjusted, positions of the light emitting portion 62 or the light absorbing member 55 (see FIG. 3) in the front end section of the needle tube 51 may be adjusted. The insertion amount of the optical fiber fixing member 77 may be adjusted in the range of the length of the first portion 71 in the optical fiber insertion direction. The length of the first portion 71 in the optical fiber insertion direction, that is, the range of adjusting the insertion amount of the optical fiber fixing member 77 is preferably longer than the length of the portion that is sharpened at an acute angle of the distal end of the needle tube 51. In this case, it is possible to arrange the light emitting portion 62 of the optical fiber 61 at any position of a portion of the distal end of the needle tube 51 which is sharpened at an acute angle.

The optical fiber insertion part 53 has an adhesive injection port 74 in order to inject an adhesive from the outside (see FIGS. 5 and 7). The adhesive injection port 74 is provided deeper than than the first portion 71 in the insertion direction of the optical fiber 61. The optical fiber fixing member 77 inserted into the first portion 71 is fixed to the inside portion of the optical fiber insertion part 53 with the adhesive injected from the adhesive injection port 74. The direction of opening the adhesive injection port 74 is not limited to this, and may be, for example, the direction perpendicular to the paper surface of FIG. 5 or 7.

The optical fiber insertion part 53 has a space 75 having an inner diameter larger than that of the first portion on a near side of the insertion direction of the optical fiber 61 than the first portion 71. As illustrated in FIG. 7, in the space 75, a portion of a protection tube (bush) 78 for protecting the optical fiber 61 is inserted in a certain range on the light source side from the optical fiber fixing member 77. The protection tube 78 is, for example, a silicone tube. In FIG. 7, the sheath 63 (see FIG. 4) for protecting the optical fiber 61 between the optical fiber fixing member 77 and the optical connector 47 is not illustrated.

Subsequently, an operation of adjusting the optical fiber insertion length in the present embodiment is described. An operator fixes the optical fiber 61 to the optical fiber fixing member 77 by an adhesive or the like at a position spaced from a distal end of the optical fiber 61. Subsequently, the optical fiber 61 is inserted into the inside portion of the needle tube 51 (see FIG. 2) from the distal end side of the optical fiber 61 through the optical fiber insertion part 53, and the optical fiber fixing member 77 is inserted into the optical fiber insertion part 53.

The operator pushes the optical fiber fixing member 77 to the first portion 71 of the optical fiber insertion part 53. The insertion length to the needle tube 51 of the optical fiber 61 is adjusted by changing a pushing amount of the optical fiber fixing member 77 to the first portion 71. The operator adjusts the insertion length of the optical fiber 61, and the light emitting portion 62 (see FIG. 3) at the distal end of the optical fiber 61 is arranged near the distal end of the needle tube 51. The optical fiber fixing member 77 is temporarily fixed to the first portion 71 by the frictional force with the protrusion 72 (see FIG. 6) in a stage of ending the adjustment.

After the operator adjusts the insertion amount of the optical fiber 61, the operator injects an adhesive from the adhesive injection port 74. The adhesive injected from the adhesive injection port 74 flows from a space 73 (see FIG. 5) in the optical fiber insertion part 53 to the first portion 71. As illustrated in FIG. 6, the first portion 71 has the three protrusion 72 at a position spaced from each other in the circumferential direction, and the adhesive flows to a gap between the optical fiber fixing member 77 temporarily fixed into the center portion of the first portion 71 and the inner wall of the optical fiber insertion part 53. In a case where the adhesive flowing to the gap is cured, the optical fiber fixing member 77 may be fixed to the optical fiber insertion part 53. After the optical fiber fixing member 77 is fixed, the operator attaches the protection tube 78 to the light source side of the optical fiber fixing member 77 and protects the end portion of the optical fiber fixing member 77 and the optical fiber 61 with the protection tube 78.

In a case where the position of the light emitting portion 62 is positioned at a desired position near the distal end of the needle tube 51, the operator fixes the light emitting portion 62 near the distal end of the needle tube 51. The light emitting portion 62 is fixed, for example, near the distal end of the needle tube 51 by the adhesive. The light absorbing member 55 (see FIG. 4) may be attached to the light emitting portion 62 before being inserted into the needle tube 51. In this case, the light absorbing member 55 may be fixed to the front end section of the needle tube 51 by an ultraviolet curing adhesive, a light curing adhesive, or a thermosetting adhesive.

Returning to FIG. 1, the probe 11 is means for detecting acoustic waves and has, for example, a plurality of ultrasonic transducers one-dimensionally arranged. The probe 11 detects the photoacoustic wave emitted from the light absorbing member 55 (see FIG. 3) after the subject is punctured with the puncture needle 15. In addition to the detection of the photoacoustic wave, the probe 11 transmits acoustic waves (ultrasonic waves) to the subject and receives reflected acoustic waves (reflected ultrasonic waves) with respect to the transmitted ultrasonic waves. The transmission and reception of the ultrasonic waves may be performed at the separated position. For example, the ultrasonic waves may be transmitted from a position different from the probe 11, and the reflected ultrasonic waves are received with the probe 11 with respect to the transmitted ultrasonic waves. The probe 11 is not limited to the linear probe and may be a convex probe or a sector probe.

The ultrasonic unit 12 includes a reception circuit 21, a reception memory 22, data separation means 23, photoacoustic image generation means 24, ultrasound image generation means 25, image synthesis means 26, control means 28, and a transmission control circuit 29. The ultrasonic unit 12 forms a signal processing device. The ultrasonic unit 12 generally has a processor, a memory, a bus, and the like. A program relating to the photoacoustic image generation is installed in the ultrasonic unit 12, and thus the processor is operated according to the program so as to realize at least a portion of the functions of the respective units in the ultrasonic unit 12.

The reception circuit 21 receives a detection signal output from the probe 11 and stores the received detection signal in the reception memory 22. The reception circuit 21 includes generally includes a low noise amplifier, a variable gain amplifier, a lowpass filter, and an Analog to Digital converter (AD converter). After the detection signal of the probe 11 is amplified by the low noise amplifier, the gain is adjusted according to the depth by the variable gain amplifier, high-frequency components are cut by the lowpass filter, and the detection signal is stored as the digital signal by the AD converter and is stored in the reception memory 22. The reception circuit 21 includes, for example, one Integrated Circuit (IC).

The reception circuit 21 stores detection signal (sampling data) of the AD-converted photoacoustic waves and the reflected ultrasonic waves in the reception memory 22. The data separation means 23 separates sampling data of the detection signal of the photoacoustic wave stored in the reception memory 22 and the sampling data of the detection signal of the reflected ultrasonic waves. The data separation means 23 inputs the sampling data of the detection signal of the photoacoustic waves to the photoacoustic image generation means 24. The sampling data of the separated reflected ultrasonic waves is input to the ultrasound image generation means (reflected acoustic wave image generation means) 25.

The photoacoustic image generation means 24 generates the photoacoustic image based on the detection signal of the photoacoustic waves detected by the probe 11. The generation of the photoacoustic image includes, for example, image reconstruction such as phase matching addition, detection, and logarithmic transformation. The ultrasound image generation means 25 generates the ultrasound image (reflected acoustic wave image) based on the detection signal of the reflected ultrasonic waves detected by the probe 11. The generation of the ultrasound image also includes image reconstruction such as phase matching addition, detection, logarithmic transformation, and the like.

The image synthesis means 26 synthesizes the photoacoustic image and the ultrasound image. The image synthesis means 26 performs image synthesis, for example, by superimposing the photoacoustic image and the ultrasound image. The synthesized image is displayed on image display means 14 such as a display device. Without performing the image synthesis, the photoacoustic image and the ultrasound image may be displayed on the image display means 14 side by side, or the photoacoustic image and the ultrasound image may be substituted and displayed.

The control means 28 controls the respective units in the ultrasonic unit 12. In a case where the control means 28 obtains, for example, the photoacoustic image, the trigger signal is transmitted to the laser unit 13 and the laser light is emitted from the laser unit 13. According to the emission of the laser light, the sampling trigger signal is transmitted to the reception circuit 21, so as to control the sampling start timing of the photoacoustic waves or the like.

In a case where the control means 28 obtains the ultrasound image, an ultrasonic transmission trigger signal is sent to instruct the transmission control circuit 29 to transmit ultrasonic waves. In a case where the ultrasonic transmission trigger signal is received, the transmission control circuit 29 transmits ultrasonic waves from the probe 11. The control means 28 sends a sampling trigger signal to the reception circuit 21 according to the timing of the transmission of the ultrasonic waves and initiates the sampling of the reflected ultrasonic waves.

According to the present embodiment, the optical fiber fixing member 77 to which the optical fiber 61 is fixed is inserted into the optical fiber insertion part 53. The optical fiber insertion part 53 has the first portion 71 into which the optical fiber fixing member 77 is inserted, and the first portion 71 has at least three protrusions protruding toward the center in the circumferential direction at positions spaced from each other. According to the present embodiment, the size of the optical fiber fixing member 77 in the direction perpendicular to the insertion direction with respect to the first portion 71 is greater than that of the inside portion of the first portion 71, and the optical fiber fixing member 77 is harder than the first portion 71. The size of the inside portion of the first portion 71 is smaller than the optical fiber fixing member 77, but the optical fiber fixing member 77 is harder than the first portion 71, and thus the optical fiber fixing member 77 may be inserted into the first portion 71. In a case where the insertion amount of the optical fiber fixing member 77 into the first portion 71 is adjusted, the distal end of the optical fiber 61 may be accurately aligned near the distal end of the needle tube 51.

According to the present embodiment, after the optical fiber insertion length is adjusted, the optical fiber fixing member 77 is fixed at the adjusted position, by using an adhesive or the like. According to the present embodiment, the size of the optical fiber fixing member 77 inserted into the first portion 71 is larger than that of the inside portion of the first portion 71. Therefore, after the adjustment of the optical fiber insertion length is completed, until the optical fiber fixing member 77 is fixed with an adhesive or the like, the optical fiber fixing member 77 is held by the frictional force working between the protrusion 72 and the optical fiber fixing member 77 in the first portion 71. Accordingly, it is possible to suppress the change of the optical fiber insertion length. According to the present embodiment, after the optical fiber insertion length is adjusted, until the optical fiber fixing member 77 is fixed, the operator does not have to hold the optical fiber 61 in order to suppress the displacement of the optical fiber 61 and the adjustment operation is simplified.

Subsequently, a second embodiment of the present invention is described. FIG. 8 illustrates a cross section of a base end section of the puncture needle according to the second embodiment of the present invention. The puncture needle according to the present embodiment further includes a metal tube 79 in which the optical fiber fixing member 77 is inserted into the inside portion. The optical fiber insertion part 53 (see FIG. 5) has a second portion 80 on a near side of the first portion 71 in the optical fiber insertion direction, in addition to the first portion 71. The size of the second portion 80 is larger than that of the first portion 71. Other points in addition to the above are the same as the first embodiment.

The metal tube 79 has a lumen to which the optical fiber fixing member 77 is inserted into the inside portion. The diameter of the lumen thereof is longer than the outside diameter of the optical fiber fixing member 77. For example, in a case where the outside diameter of the optical fiber fixing member 77 is about 1.4 mm, the diameter of the lumen of the metal tube 79 is set to be about 1.6 mm. The second portion 80 is a portion into which the metal tube 79 is inserted. The inner diameter of the second portion 80 is set to be almost the same size as the outside diameter of the metal tube 79 or smaller than the outside diameter of the metal tube 79. The metal tube 79 is pushed, for example, to the second portion 80. The metal tube 79 is fixed to the optical fiber insertion part 53 with the frictional force working between the metal tube 79 and the inner wall of the second portion 80. In the second portion 80, the frictional force working the inner wall thereof and the metal tube 79 is greater than the frictional force working the optical fiber fixing member 77 and the protrusion 72 in the first portion 71.

Before inserting the optical fiber 61 from the optical fiber insertion part 53 to the needle tube 51 (see FIG. 2), the operator inserts the metal tube 79 to the second portion 80 of the optical fiber insertion part 53. Subsequently, the operator inserts the optical fiber 61 to the needle tube 51 through the optical fiber insertion part 53 into which the metal tube 79 is inserted. The insertion of the optical fiber fixing member 77 into the first portion 71 is the same as described in the first embodiment.

After adjusting the insertion amount of the optical fiber fixing member 77, the operator injects an adhesive toward a gap between the metal tube 79 and the optical fiber fixing member 77 from the end portion on the light source side of the metal tube 79. Accordingly, the optical fiber fixing member 77 is instantly fixed to the metal tube 79. The operator injects an adhesive from the adhesive injection port 74 and fixes the optical fiber fixing member 77 to the first portion 71. Generally, the strength of the adhesiveness between metal by the adhesive is higher than the adhesive strength between the resin and the metal. In a case where the optical fiber fixing member 77 is formed of metal, the adhesive strength between the optical fiber fixing member 77 and the metal tube 79 is higher than that between the optical fiber fixing member 77 and the first portion 71. After fixing the optical fiber fixing member 77, the operator attaches the protection tube 78 to the light source side than the optical fiber fixing member 77 and protects the end portion of the optical fiber fixing member 77 and the optical fiber 61 with the protection tube 78.

The puncture needle according to the present embodiment has the metal tube 79. The metal tube 79 is inserted into the optical fiber insertion part 53, and the insertion of the optical fiber 61 into the needle tube 51 and the insertion of the optical fiber fixing member 77 into the first portion of the optical fiber insertion part 53 are performed through the metal tube 79. After the insertion amount of the optical fiber fixing member 77 into the first portion 71 is adjusted, the optical fiber fixing member 77 is firmly fixed to the metal tube 79 by using an instantaneous adhesive or the like, and thus it is possible to use a stable adhesive or the like although more time is required for curing at other bonding regions. In a case where the adhesive injected to the first portion 71 is cured and then stopped by the metal tube 79, the optical fiber fixing member 77 may be firmly fixed. Since the metal tube 79 may be firmly fixed for a short period of time, the frictional force between the optical fiber fixing member and the first portion 71 is set to be lower than the case of the first example, such that in a case where the front end section of the optical fiber 61 is adjusted, the fine adjustment may be performed with the smaller force. Other effects are the same as those of the first embodiment.

As an assembling method according to the derivative form of the above embodiment, there is an assembling method using an indirect fixing method of temporarily fixing the optical fiber fixing member 77 to the sheath 63 through the sheath 63 and fixing the sheath 63 and the optical fiber 61. That is, the optical fiber fixing member 77 once passes a position slightly beyond the end portion of the sheath 63. Subsequently, at a position which the optical fiber fixing member 77 passes slightly beyond the end portion of the sheath 63, for example, the optical fiber fixing member 77 is caulked by using pliers or the like to an extent that the optical fiber 61 does not break. The position at which the optical fiber fixing member 77 is caulked is, for example, a portion near the end portion of the optical fiber fixing member 77 on the light source side. In this caulking step, the optical fiber fixing member 77 and a portion of the sheath 63 comes into contact with each other, the position of the sheath 63 (that is, the front end section of the optical fiber 61) may be adjusted while the frictional force is obtained. In this state, the optical fiber fixing member 77 is inserted into the first portion 71.

According to the assembling method according to the derivative form of the above embodiment, two kinds of frictional force: the first frictional force between the optical fiber fixing member 77 and the first portion 71 and the second frictional force between the optical fiber fixing member 77 and the sheath 63 may be used. With respect to the effects, for example, in a case where the unevenness of the first frictional force is greater than the tolerance of resin form, after the position of the optical fiber fixing member 77 with respect to the first portion 71 is roughly adjusted, the displacement of the sheath 63 with respect to the optical fiber fixing member 77 may be finely adjusted by using the second frictional force smaller than the first frictional force.

This contributes to the stabilization and/or the efficiency of the assembly process. As the assembling method after the fiber insertion amount is adjusted, those described in the first embodiment or the second embodiment may be appropriately employed.

In the respective embodiments, it is described that the probe 11 detects both of the photoacoustic waves and the reflected ultrasonic waves, but the probe used in the generation of the ultrasound image and the probe used in the generation of the photoacoustic image may not be the same. The photoacoustic waves and the reflected ultrasonic waves may be respectively detected by independent probes. Any one of the detection (sampling) of the photoacoustic wave and the detection (sampling) of the reflected ultrasonic waves may be performed first.

The puncture needle is not limited to the application of percutaneously puncturing the subject from the outside of the subject, but may be a needle for an ultrasonic endoscope. The optical fiber 61 and the light absorbing member 55 are provided on a needle for an ultrasonic endoscope, the light absorbing member 55 provided in the front end section of the needle is irradiated with light, and the photoacoustic wave is detected, so as to generate the photoacoustic image. In this case, puncturing may be performed while the position of the front end section of the needle for the ultrasonic endoscope is confirmed by observing the photoacoustic image. The photoacoustic wave generated in the front end section of the needle for the ultrasonic endoscope may be detected by using a body surface probe or may be detected using a probe incorporated in the endoscope.

Figure 9:
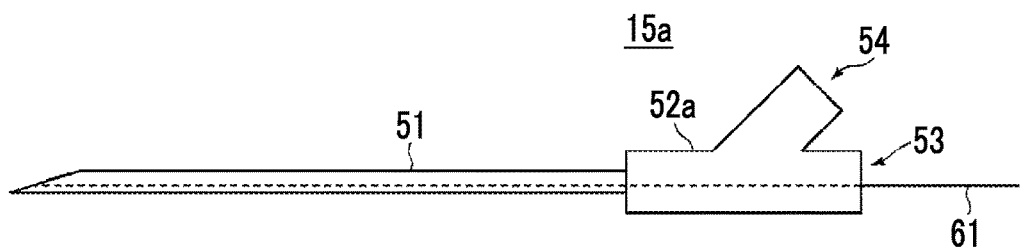
FIG. 9 is a side view illustrating a puncture needle according to a first deformation example.

In FIG. 2, an example in which the optical fiber insertion part 53 is inclined with respect to the axial direction of the needle tube 51, and the optical fiber 61 is inserted into the base end section 52 at an angle inclined with respect to the axial direction of the needle tube 51 is described, but the present invention is not limited thereto. The positional relationship between the optical fiber insertion part 53 and the medicine injection portion 54 is not limited to that illustrated in FIG. 2, and any positional relationship is allowed. FIG. 9 illustrates a puncture needle according to a first deformation example. A base end section 52a of a puncture needle 15a has the optical fiber insertion part 53 on an extension line in the axial direction of the needle tube 51, and the medicine injection portion 54 is inclined with respect to the axial direction of the needle tube 51. Also in this case, the insertion length of the optical fiber 61 may be adjusted by displacing the optical fiber fixing member 77 inserted into the optical fiber insertion part 53.

According to the respective embodiments, an example in which the puncture needle 15 has the medicine injection portion 54 in the base end section 52 is described, but the puncture needle 15 may not have to have the medicine injection portion 54. In this case, the inside portion of the needle tube 51, particularly, the front end section thereof, may be may be closed after the insertion of the optical fiber 61.

Figure 10A:
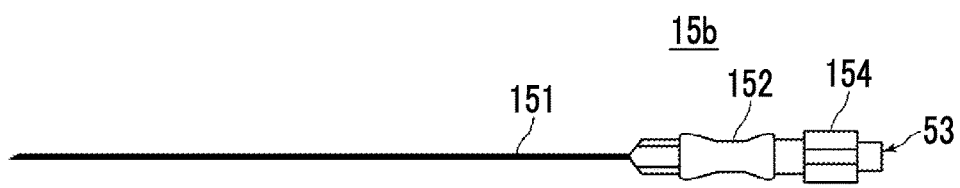
FIG. 10A is a diagram illustrating an external appearance of an entire puncture needle of a second deformation example.
Figure 10B:
FIG. 10B is a diagram illustrating an external appearance of an outer needle.
Figure 10C:
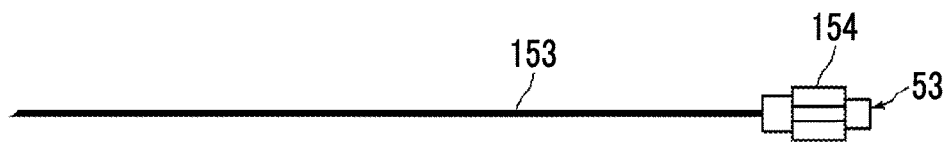
FIG. 10C is a diagram illustrating an external appearance of an inner needle.

The puncture needle 15 may have an inner needle and an outer needle. FIGS. 10A, 10B, and 10C illustrate a puncture needle 15b according to the second deformation example. FIG. 10A illustrates an external appearance of the entire puncture needle, FIG. 10B illustrates an external appearance of the outer needle, and FIG. 10C illustrates an external appearance of the inner needle. The puncture needle 15b has an outer needle 151 and an inner needle 153. The outer needle 151 has a lumen in the inside portion. The inner needle 153 has the outside diameter which is, for example, almost the same as the inner diameter of the outer needle 151, and is formed so as to be capable of being pulled in and out from the hollow outer needle 151. The outer needle 151 adheres to an outer needle base 152 (see FIG. 10B), and an inner needle 153 adheres to an inner needle base 154 (see FIG. 10C). The inner needle base 154 has the optical fiber insertion part 53, and the optical fiber 61 (see FIG. 2) is inserted into the inside portion of the inner needle 153.

The inner needle 153 is inserted from the outer needle base 152 side into the lumen of the outer needle 151, and at least a portion of the lumen of the outer needle 151 is sealed to an extent of preventing the intrusion of a piece of the living body or the like to the lumen. In the inner needle base 154, a protrusion portion for aligning the connection position is provided, and a groove to be engaged with the protrusion portion of the inner needle base 154 is provided in the outer needle base 152. In a case where the inner needle 153 is set in the outer needle 151, the positions the protrusion of the inner needle base 154 and the groove of the outer needle base 152 are aligned, and then the inner needle base 154 is engaged with the outer needle base 152.

Figure 11:
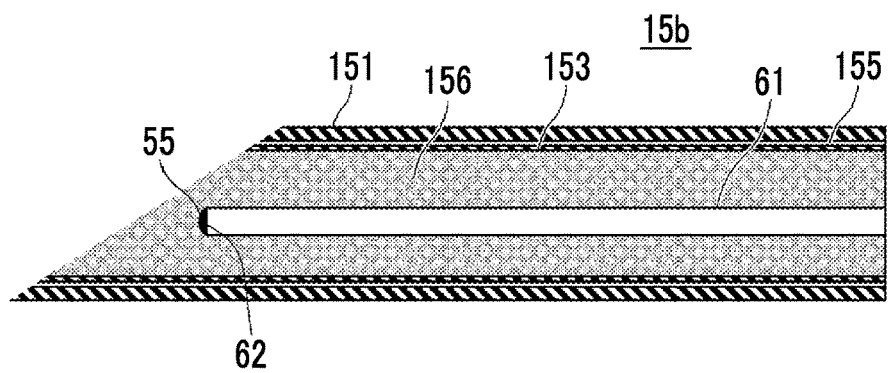
FIG. 11 is a cross sectional view illustrating a distal end of a puncture needle according to the second deformation example.

FIG. 11 illustrates a cross section near the distal end of the puncture needle 15b according to a second deformation example. The front end sections of the outer needle 151 and the inner needle 153 are sharpened at an acute angle. The inner needle 153 has a tube 155 forming the needle tube. The optical fiber 61 is inserted into the tube of the tube 155. In the inside portion of the tube 155, the light emitting portion 62 of the optical fiber 61 is covered with the light absorbing member 55. Instead of covering the light emitting portion 62 with the light absorbing member 55 after the insertion of the optical fiber 61, the optical fiber 61 may be inserted into the tube of the tube 155 after the light emitting portion 62 is covered with the light absorbing member 55. The positions of the light emitting portion 62 and the light absorbing member 55 may be adjusted with respect to the distal end (opening) of the tube 155, by adjusting the insertion length of optical fiber into the inner needle 153 (the tube 155). After the insertion length of the optical fiber 61 is adjusted, the inside portion of the tube 155 is filled with a transparent resin 156, and the optical fiber 61 is buried in the inside portion of the tube 155. For example, a soft epoxy resin with less damping of the acoustic waves is used as the transparent resin 156.

The subject is punctured with the puncture needle 15b in a state in which the inner needle 153 is set in the outer needle 151 (see FIG. 10A). Since the lumen of the outer needle 151 is closed with the inner needle 153, it is possible to prevent a flesh piece or the like from being caught in the course of performing puncturing with the needle, and thus the hinderance of sense of the piercing by the operator may be prevented. Moisture may be prevented from flowing from the puncture region to the lumen of the outer needle 151. After puncturing the subject, the operator releases the connection between the inner needle base 154 and the outer needle base 152 and removes the inner needle 153 from the outer needle 151. After removing the inner needle 153, the operator mounts a syringe or the like to the outer needle base 152 and injects a medicine such as an anesthetic. Otherwise, the operator takes a biopsy sample from a place of the subject which is punctured with the puncture needle 15b.

According to the respective embodiments, the puncture needle is considered as the insert, but the present invention is not limited thereto. The insert may be a catheter to be inserted into the blood vessel. The insert may be an indwelling needle. In the respective embodiments, a needle having an opening at the distal end is assumed as the needle, but the opening does not have to be provided at the front end section. The needle is not limited to a needle such as an injection needle and may be a biopsy needle used for biopsy. That is, the biopsy needle may be a biopsy needle capable of collecting a tissue of a biopsy region in an examination target by puncturing the examination target of a living body. The needle may also be used as a guiding needle for puncturing the deep portion, such as a blood vessel, subcutaneous, or internal organs inside the belly.

In FIG. 2, the needle tube 51 and the base end section 52 do not have to be formed in an inseparable manner, and the portion of the needle tube 51 and the portion of the base end section 52 may be formed in a separable manner. For example, the portion of the base end section 52 connected to the needle tube 51 is set to have a screw structure of being coupled (engaged) with a commercially available needle (needle tube), and any needles may be attachable to the base end section 52. In this case, the portion of the base end section 52 may be set as an attachment member that is engageable with the needle tube (hollow tube). In a case where the needle tube is formed to be in replaceable manner, it is preferable that a light absorbing member is attached to the optical fiber in advance. The operator or the like inserts a separately prepared needle into the attachment member (base end section) and adjusts the insertion amount of the optical fiber fixing member 77 (see FIG. 7 and the like) into the first portion 71, so as to adjust the position of the light absorbing member at a distal end of the needle. In this manner, it is possible to assemble a needle having a function capable of confirming the distal end position of the needle with ultrasonic waves immediately before the operation.

Figure 12:
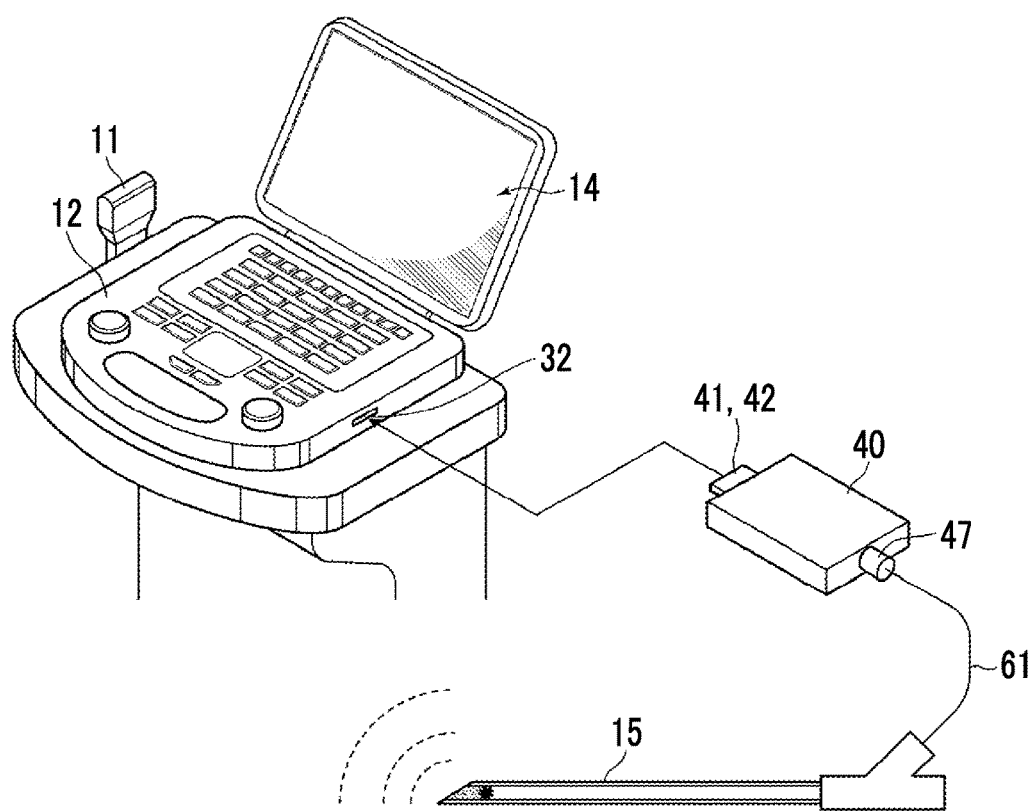
FIG. 12 is a perspective view illustrating an external appearance of a photoacoustic image generating device.

Finally, FIG. 12 illustrates the external appearance of the photoacoustic image generating device. The probe 11 is connected to the ultrasonic unit 12. The ultrasonic unit 12 is formed as an integrated device including the image display means 14. The ultrasonic unit 12 generally has a processor, a memory, a bus, and the like. A program relating to the generation of the photoacoustic image is incorporated to the ultrasonic unit 12. A laser unit 40 corresponds to the laser unit 13 of FIG. 1.

The ultrasonic unit 12 has a port 32 having a trigger signal port and a power supply port. A connector including a power supply input terminal 41 and a trigger input terminal 42 of the laser unit 40 is inserted into the port 32. In a case where the laser unit 40 is formed as a card-sized and light-weighted small device, the laser unit 40 may be held by being inserted into the port 32 of the ultrasonic unit 12. A cable including a trigger signal and a power supply line comes out from the laser unit 40 and may be connected to the ultrasonic unit 12.

The optical connector 47 connected to a light output terminal of the laser unit 40 is arranged at one end of the optical fiber 61 forming the light guiding member of the puncture needle 15. Instead of the arrangement of the optical connector 47, the optical fiber 61 is inserted into the light output terminal without change and held by a spring force or the like. In a case where strong force is applied to the light output terminal due to the pulling of the puncture needle 15 by the operator, it is possible to prevent the optical fiber 61 from being fallen out from the light output terminal such that the optical fiber 61 breaks. In a case where the optical fiber 61 is formed to be directly inserted into and pulled out from the light output terminal, the optical connector 47 does not have to be provided in the optical fiber extending from the puncture needle 15, and there is an effect of reducing the cost.

The pulse energy of the pulsed laser light output from the laser unit 40 may be 6.4 µJ in a case where the core diameter of the optical fiber 61 is 200 µm. In a case where the core diameter of the optical fiber 61 is 100 µm, the pulse energy may be 2.0 µJ. The pulse time width may be set to 80 ns.

In FIG. 12, the light output terminal is provided on the surface facing the surface on which the port 32 is present, but the light output terminal is preferably provided on the surface orthogonal to the surface on which the port 32 is present. In a case where the light output terminal is provided on the facing surface, in a case where the laser unit 40 is pulled in a case where the operator moves the puncture needle 15, the laser unit 40 is fallen out from the port 32 in some cases. In contrast, in a case where the light output terminal is provided on the orthogonal surface, even in a case where the laser unit 40 is pulled, the laser unit 40 is hardly fallen out from the port 32.

The trigger input signal and the power supply line may not be the same cable, and the trigger input terminal 42 may obtain a trigger signal from, for example, a connector for Electrocardiogram (ECG) synchronization which is attached to a general ultrasonic system. The power terminal may be taken out from the USB terminal. Otherwise, a trigger signal may be obtained from the terminal of a portion of the connector of the probe.

The present invention is described above based on the preferable embodiments thereof, but the insert and the attachment member of the present invention are not limited to the above embodiments, and various modifications and changes from the above embodiments are included in the scope of the present invention.

What is claimed is:

1. An insert comprising:
    a hollow tube of which at least a portion is inserted into a subject;
    an optical fiber that is inserted into an inside portion of the hollow tube and guides light emitted from a light source;
    a base end section including an optical fiber insertion part used for inserting the optical fiber;
    a light absorbing member that absorbs light guided by the optical fiber in a case of being irradiated with the light and generates a photoacoustic wave;
    an optical fiber fixing member that fixes the optical fiber at a position spaced from a distal end of the optical fiber and is inserted into the optical fiber insertion part,
    wherein the optical fiber insertion part includes a first portion into which the optical fiber fixing member is inserted and which has at least three protrusions protruding toward the center at positions spaced from each other in a circumferential direction, and
    a size of the optical fiber fixing member in a direction perpendicular to an insertion direction into the first portion is larger than that of an inside portion of the first portion, and the optical fiber fixing member is fixed by the at least three protrusions of the first portion.

2. The insert according to claim 1,
    wherein a size of a cross section of the optical fiber fixing member in the direction perpendicular to the insertion direction is larger than that of a diagram that is circumscribed with the at least three protrusions and is similar to a shape of the cross section of the optical fiber fixing member in the direction perpendicular to the insertion direction.

3. The insert according to claim 1,
    wherein the optical fiber insertion part has an axis extending along a predetermined direction, and an insertion amount of the optical fiber fixing member into the first portion in the direction of the axis is capable of being adjusted.

4. The insert according to claim 1,
    wherein the at least three protrusions extend along the insertion direction of the optical fiber.

5. The insert according to claim 1,
    wherein the optical fiber insertion part further includes an adhesive injection port provided deeper than the first portion in the insertion direction of the optical fiber.

6. The insert according to claim 5,
    wherein the optical fiber fixing member is fixed in the optical fiber insertion part with an adhesive injected from the adhesive injection port.

7. The insert according to claim 1,
    wherein Young's modulus of the optical fiber fixing member is the same as that of the first portion or higher than that of the first portion.

8. The insert according to claim 1,
    wherein the optical fiber fixing member is formed of at least one of a metallic material, a hard resin, or a ceramic material.

9. The insert according to claim 1,
    wherein the at least three protrusions is formed of a resin material.

10. The insert according to any claim 1, further comprising:
    a metal tube into which the optical fiber fixing member is inserted.

11. The insert according to claim 10,
    wherein the optical fiber insertion part includes a second portion having a size larger than the size of the optical fiber fixing member on a near side of the first portion in the insertion direction of the optical fiber, and the metal tube is inserted into the second portion.

12. The insert according to claim 10,
    wherein a size of the inside portion of the metal tube is larger than the size of the optical fiber fixing member.

13. The insert according to claim 1,
    wherein the hollow tube has an opening at a distal end, and the distal end of the hollow tube is sharpened at an acute angle.

14. The insert according to claim 13,
    wherein a length of the first portion in the insertion direction of the optical fiber is longer than that of the portion of the distal end of the hollow tube which is sharpened at an acute angle.

15. An attachment member which is engageable with a hollow tube of which at least a portion is inserted into a subject, the attachment member comprising:
    an optical fiber that is inserted into an inside portion of the hollow tube in a case where the hollow tube is engaged and guides light emitted from a light source;
    a base end section including an optical fiber insertion part used for inserting the optical fiber; and
    an optical fiber fixing member that fixes the optical fiber at a position spaced from a distal end of the optical fiber and is inserted into the optical fiber insertion part,
    wherein the optical fiber insertion part includes a first portion into which the optical fiber fixing member is inserted and which has at least three protrusions protruding toward the center at positions spaced from each other in a circumferential direction, and
    a size of the optical fiber fixing member in a direction perpendicular to an insertion direction into the first portion is larger than that of an inside portion of the first portion, and the optical fiber fixing member is fixed by the at least three protrusions of the first portion.

* * * * *